(12) United States Patent
Rotenberg

(10) Patent No.: US 8,271,077 B1
(45) Date of Patent: *Sep. 18, 2012

(54) LEARNING OPTIMIZATION USING BIOFEEDBACK

(75) Inventor: Eduard Rotenberg, Groton, MA (US)

(73) Assignee: Lockheed Martin Corporation, Bethesda, MD (US)

( * ) Notice: Subject to any disclaimer, the term of this patent is extended or adjusted under 35 U.S.C. 154(b) by 358 days.

This patent is subject to a terminal disclaimer.

(21) Appl. No.: 12/548,056

(22) Filed: Aug. 26, 2009

Related U.S. Application Data

(60) Provisional application No. 61/092,362, filed on Aug. 27, 2008.

(51) Int. Cl.
*A61B 5/04* (2006.01)
(52) U.S. Cl. ........................................ 600/545; 600/301
(58) Field of Classification Search .................. 600/544, 600/545
See application file for complete search history.

(56) References Cited

U.S. PATENT DOCUMENTS

| | | | | |
|---|---|---|---|---|
| 4,533,346 | A | * | 8/1985 | Cosgrove et al. ............... 604/66 |
| 5,724,987 | A | * | 3/1998 | Gevins et al. .................. 600/544 |
| 6,626,676 | B2 | * | 9/2003 | Freer ............................. 434/236 |
| 2004/0152995 | A1 | * | 8/2004 | Cox et al. ....................... 600/544 |
| 2008/0220400 | A1 | * | 9/2008 | Cox et al. ....................... 434/236 |
| 2008/0275358 | A1 | * | 11/2008 | Freer et al. .................... 600/544 |

OTHER PUBLICATIONS

"CNN Review: 'Madden NFL 09' is a must-buy", *Associated Press*, (Retrieved Aug. 11, 2008), 3 pgs.
Engel, R S, et al., "Toward a better understanding of racial and ethnic disparities in search and seizure rates", *Journal of Criminal Justice*, 34(6), 605-617.
Lee, V E, et al., "Effects of school restructuring on the achievement and engagement of middle-grade students", *Sociology of Education*, 66, (1993), 164-187.
Mills, C. N, et al., "Chapter 4—The GRE Computer Adaptive Test: Operational Issues", *In: Computerized Adaptive Testing: Theory and Practice*, Norwell, MA: Kluwer Academic Publishers, W. J. V. d. Linden & C. A. W. Glas (Eds.), (2000), 75-99.
Poythress, M, et al., "Correlation Between Expected Workload and EEG Indices of Cognitive Workload and Task Engagement", *In D.D. Stanney & L. A. Reeves (Eds.), Foundations of Augmented Cognition*, 2nd edition, Arlington, VA: Strategic Analysis, Inc., (2006), 32-44.
Reeve, J, et al., "Enhancing Students' Engagement by Increasing Teachers' Autonomy Support", *Motivation and Emotion*, 28(2), (Jun. 2004), 147-169.
Smith, K A, et al., "Pedagogies of engagement: classroom-based practices", *Journal of Engineering Education, Special Issue on the State of the Art and Practice of Engineering Education Research*, 94(1), (2005), 15 pgs.

* cited by examiner

*Primary Examiner* — Michael Kahelin
*Assistant Examiner* — Eric Messersmith
(74) *Attorney, Agent, or Firm* — Schwegman, Lundberg & Woessner, P.A.

(57) ABSTRACT

A system includes a sensor to detect a neuro-physiological state of a student, and a controller to provide a communication if the student is outside a desired neuro-physiological state consistent with a desired learning zone and to provide a lesson intensity control signal as a function of the provided communication and sensed neuro-physiological state.

19 Claims, 3 Drawing Sheets

LEARNING OPTIMIZATION USING BIOFEEDBACK

RELATED APPLICATION

This application claims priority to U.S. Provisional Application Ser. No. 61/092,362 (entitled Adaptive Biofeedback Enhanced Learning And Training Systems, filed Aug. 27, 2008) which is incorporated herein by reference.

BACKGROUND

Prior learning systems have attempted to use electric signals, such as electroencephalogram signals to control the difficulty of the material presented to a student. Such systems have had some success in improving the efficiency of learning. However, there is a need to further improve the efficiency of learning.

SUMMARY

A system and method utilize a measured neuro-physiological state of a student to provide both self regulation feedback and learning intensity feedback to optimize a learning experience.

DETAILED DESCRIPTION

In the following description, reference is made to the accompanying drawings that form a part hereof, and in which is shown by way of illustration specific embodiments which may be practiced. These embodiments are described in sufficient detail to enable those skilled in the art to practice the invention, and it is to be understood that other embodiments may be utilized and that structural, logical and electrical changes may be made without departing from the scope of the present invention. The following description of example embodiments is, therefore, not to be taken in a limited sense, and the scope of the present invention is defined by the appended claims.

The functions or algorithms described herein may be implemented in software or a combination of software and human implemented procedures in one embodiment. The software may consist of computer executable instructions stored on computer readable media such as memory or other type of storage devices. Further, such functions correspond to modules, which are software, hardware, firmware or any combination thereof. Multiple functions may be performed in one or more modules as desired, and the embodiments described are merely examples. The software may be executed on a digital signal processor, ASIC, microprocessor, or other type of processor operating on a computer system, such as a personal computer, server or other computer system.

A system and method utilize a measured neuro-physiological state of a student to provide both self regulation feedback and learning intensity feedback to optimize a learning experience. In various embodiments, sensors may be used to provide signals representative of the neuro-physiological state of the student, and such signals are converted to digital representations corresponding to whether the student is in a desired learning zone. Self-regulation feedback may be provided to the student to allow the student to modify their own behavior to return to a desired learning zone. In addition, lesson intensity values may be modified based on a current state of the student and historical state. The lesson intensity values may then be used to control the intensity of a learning experience being provided to the student. The system provides adaptive and accelerated training by customizing a training experience to an individual's neurological and physiological response. Better training may be provided in a faster, lower cost manner. Instructors have a direct indication of off-task students. Instructors may also be remote from students.

The system and method may be used in many different learning environments, such as in flight simulators and other virtual environments, training systems, class rooms with instructors, military training exercises, systems for treatment of post traumatic stress disorder (PTSD), system for rehabilitation traumatic brain injury patients and many other training environments.

Figure 1:
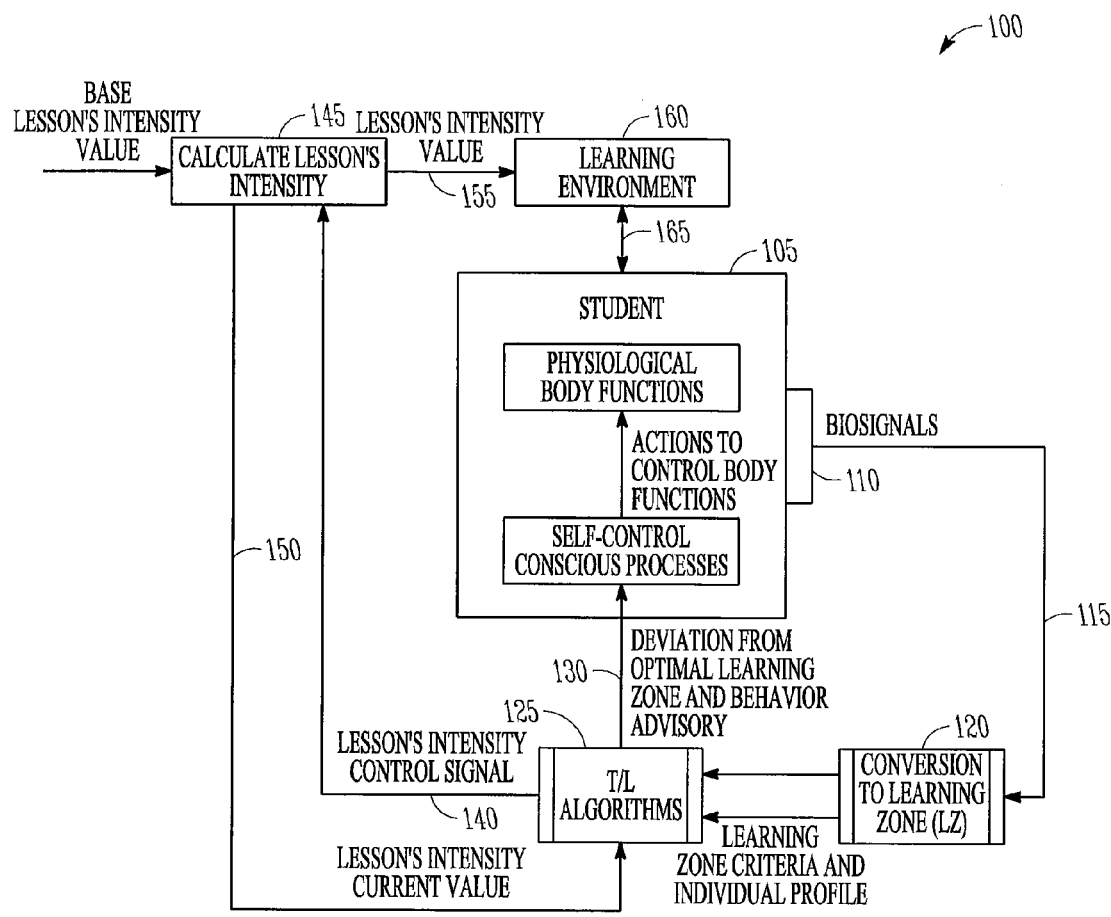
FIG. 1 is a block diagram of a learning system utilizing biofeedback according to an example embodiment.

FIG. 1 is a block diagram of a system 100 that provides a measured neuro-physiological state of a student to provide both self regulation feedback and learning intensity feedback to optimize a learning experience. In one embodiment, the system may be referred to as an adaptive biofeedback enhanced learning and training system (ABELTS). A student 105 in one embodiment is monitored by a sensor 110. In various embodiments, sensor 110 may measure multiple neuro-physiological states of the student 105, such as a physiological/psychological state that may include cognitive workload. Sensor 110 in one embodiment includes one or more sensors such as an electroencephalograph (EEG), electrocardiograph (ECG), galvanic skin response (GSR), heart rate variability (HRV), pupilometry, etc. Multiple sensors may be used to decrease noise/signal ratio and improve pattern recognition.

Signals from the sensor 110, are provided at 115 to a conversion to learning zone parameters converter 120, which converts the signals to a digital format corresponding to a learning zone. A learning zone may be defined as function of a student's neuro-physiological parameters and range of values for such parameters, where learning is optimal. Deviation from the range may reduce speed and quality of learning. The neuro-physiological output 115 from the student 105 is converted to student cognitive parameters, such as level of cognitive workload, level of engagement, alertness, visual engagement, focus, distraction, drowsiness, level of cognitive fatigue, etc. Patterns of the output 115 may be correlated to previous known patterns of an individual student, or even from a group of students to determine the cognitive state of the user to determine whether the student 105 is functioning within a desired learning zone. Such correlation in one embodiment may be done by a controller 125 that is coupled to receive the digital output of converter 120.

Controller 125 in one embodiment performs the above pattern recognition to determine the cognitive/neuro-physiological state of the student 105. In one embodiment, the patterns may comprise up to 10 or more dimensions of neuro-physiological parameters. Other algorithms may be used, such as lookup tables indexed by the digital values, or equations developed based on a history of collected data for individual students or groups of students.

A first feedback loop is indicated at 130. The state may be presented to the student 105 via feedback loop 130, allowing the student to understand what state they are in and use self control in an attempt to alter their state. The controller 125 may provide the state information in the form of a communication, such as visual text, symbols, sound, or other physical stimulus if desired. In addition, the communication may provide suggestions, such as breathing exercises, relaxation techniques, or other suggestions based on standard known self regulation techniques or student specific techniques that have worked. In one embodiment, the communication may just tell the student to "wake up", or "concentrate". Such communications in one embodiment may be provided based on alpha/beta ratios from EEC sensors.

Controller 125 also utilizes the physiological/psychological state signals to determine the cognitive state corresponding to the user's position in relation to the learning zone, and to derive a lesson intensity control signal as indicated at 140. The lesson intensity control signal may have a value indicating that the lesson intensity should be decreased or increased depending on the change in learning zone over time and whether the student responded to the feedback 130. In one embodiment, the lesson intensity control signal is provided to a module 145 that calculates lesson intensity, then either keeping it the same, decreasing it, or increasing it. It also provides the current lesson intensity value back to the controller 125 via 150.

The lesson intensity value is provided from module 145 via 155 to a learning environment 160, completing a second feedback loop 155. The learning environment 160 is representative of any environment where learning is desired. Learning environment 160 includes virtual environments, such as flight simulators, class rooms with one or more students and a teacher, field exercises, etc. The lesson intensity value may be processed to change the speed of the learning experience, change the difficulty of material presented, change the volume or brightness, or control any other controllable parameter of the learning environment to optimize a learning experience.

Generally, if a student is found to be in an optimal learning zone, more material may be learned, and the lesson intensity value may be increased until the user begins to transition out of the optimal learning zone. As the user begins to transition out of the optimal learning zone, the first feedback loop 130 may be used to attempt to keep the user in the optimal learning zone prior to decreasing lesson intensity. The use of the first feedback loop 130 and second feedback loop 155 may provide an optimized learning experience.

In one embodiment, feedback loop 130 shows student 105 that their parameters deviate from their optimal learning zone, defined as a subset in the individual student's multidimensional physiological/psychological space. The system 100 may suggest actions to try to correct the observable deviation, if any, by having the student use advance self-regulating strategies. Lesson intensity may be automatically corrected via a set of intelligent adaptive algorithms based on information from captured real-time training feedback and the student's real-time deviation from the optimal learning zone.

In one example situation where system 100 senses that a student's measure of cognitive workload is not optimal, the system 100 will consider the student's physiological/psychological state in relation to his or her own optimal learning zone, and the history/current state of the student's attempts to stay inside that zone. Based on this information, the system 100 will adjust the lesson by either increasing or decreasing the intensity of the lesson to bring the student into their optimal learning zone.

During training, students may acquire habits of self-regulation, such as the early recognition the symptoms of deviation from optimal learning zone/stress/mental fatigue, together with the application of corresponding mitigation strategies.

In some embodiments, the system may use task and user-independent algorithms to convert physiological data into multiple gauge readings, which show second by second variations in mental activity. These mental state gauges, which currently include cognitive workload, distraction, engagement, and drowsiness, provide insight into an individual's mental processing. The system thus provides objective measures at a rate of once per second that show mental state(s) without interrupting performance.

Figure 2:
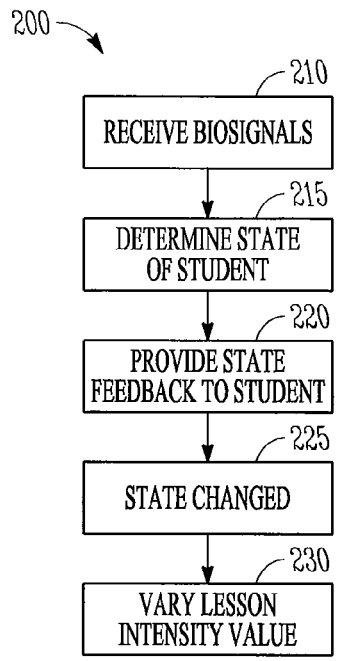
FIG. 2 is a flowchart indicating a method of providing multiple levels of feedback in a learning environment according to an example embodiment.

A method for optimizing training is shown generally at 200 in flowchart form in FIG. 2. In one embodiment, the method 200 is implemented by a computer system. At 210, biosignals representative of a neuro-physiological state of a student are received. A current neuro-physiological state is determined at 215 using the received biosignals. In various embodiments, the biosignals include many different measurements of physiological and psychological state of the student. At 220, feedback is provided to the student as a function of the neuro-physiological state of the student as determined from the biosignals. If the neuro-physiological state of the student has changed as indicated at 225 following provision of the feedback, further feedback may be provided by modifying a lesson intensity value as a function of the neuro-physiological state of the student at 230 and providing the modified lesson intensity value to the learning environment 160.

Several variations may be seen in further embodiments. If the student maintains an optimal learning cognitive state, no feedback may be provided. Alternatively, the student may be provided feedback about his or her cognitive state so that they understand they are in a good state. The intensity level may also be manipulated in some embodiments such that it gradually increases to further optimize the learning experience. The gradual increase may continue until a detrimental change in the cognitive state is detected, at which point cognitive state feedback may be provided to the user followed by a reduction in intensity if the detrimental change in cognitive state does not improve. Alternatively, if the cognitive state feedback worked to return the student to an optimal learning cognitive state, the intensity may again be increased, or held constant if desired.

In further embodiments, natural biorhythms of students may be taken into account in both determining the cognitive state of the student and in providing cognitive state feedback and learning intensity feedback. Providing both types of feedback enables the use of many different control algorithms which may utilize one or more biosignals. Great flexibility in the algorithms may be provided in various embodiments.

Figure 3:
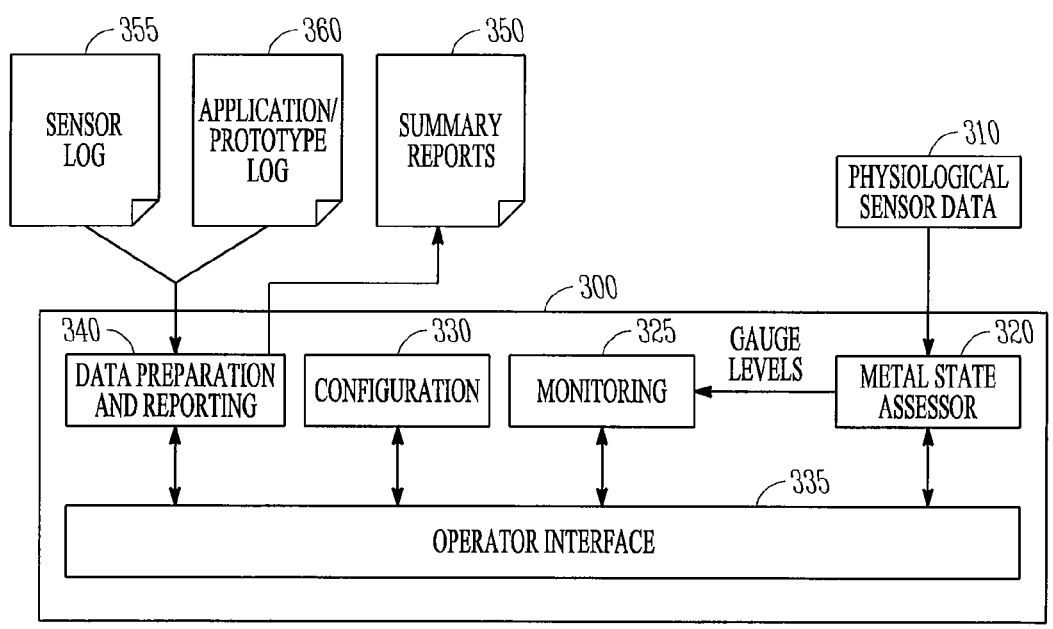
FIG. 3 is a block architectural diagram of a mental state assessor according to an example embodiment.

FIG. 3 is a block diagram of a sensor based mental assessment system 300 according to an example embodiment. Physiological sensor data is generated or received at 310 and provided to the system 300. In various embodiments, the sensor data may include one or more of EEG, EKG, GSR and pupilometry. Other sensors may be used in further embodiments, such as body temperatures, oxygen levels, blood sugar levels, and many others if desired.

System 300 includes a mental state assessor 320 that receives the sensor data and assesses the mental state represented by the sensor data. The mental state may be determined by many different algorithms, including the use of empirical observations of students and correlating such observations to the sensor data. The mental state may be tailored to each individual student in one embodiment. Mental state gauges may be provided at a monitoring module 325, which may provide graphical indications of different mental states, such as cognitive workload, visual engagement, distraction, drowsiness and others. At 330, the system 300 may be configured to allow operators, via an operator interface 335 to manually enter non-logged events in real time. Many different data preparation and reporting functions may be available as indicated at 340 to provide summary reports 350, sensor logs 355 and application/prototype logs 360. In one embodiment, a real-time estimate of cognitive workload may be provided.

In one embodiment, learning optimization is provided based on student's state of cognitive workload value W(t), t-time.

Intensity of lessons is a function of the number of tasks given to a student per a certain time period. A new set of tasks appears on the screen after the time period expires. In one example, there may be 10 levels of intensity. Level one consists of a single task; level two consists of two tasks, and so on.

For calculating student's state of cognitive workload, a set of EEG sensors may be placed on student's scalp. A raw EEG signal, polled with frequency 256 Hz, after filtration and removal artificial effects (e.g., eyes blinking), is converted to values of amplitudes for different frequencies by using a FFT (Fast Fourier Transformation) algorithm.

In one embodiment, the following standard frequencies: $\alpha$ is in the range 8-12 Hz, $\beta$ is the range of 12-30 Hz, $\gamma$ is the range of 30-100 Hz, B is the range of 4-7 Hz and $\delta$ is the range 0-4 Hz may be used. Conversion to a value of workload W (t) may be done according to the following formula:

$$W(t-n) = k_1\alpha(t-n) + k_2\beta(t-n) + k_3\gamma(t-n) + k_4\theta(t-n) + k_4\delta(t-n) + k_5\alpha(t-n)/\theta(t-n) + k_6\gamma(t-n)/\alpha(t), n=0, 1, 2, \ldots, m$$

$$W(t) = \sum_{i=0}^{m} r_i W(t-i) \quad (1)$$

Where—$k_i$—conversion coefficients for different frequencies $\alpha(t), \beta(t), \gamma(t), \theta(t), \delta(t)$; $r_i$—weight coefficients.

For regulation lesson's intensity level a proportional integral controller may be used:

$$Y(n) = k_1(W(n) - W_{set}) + \sum_{i=0}^{n} k_2(W(i) - W_{set}) \quad (2)$$

Where Y(n) corresponds to a lesson's intensity on step n, W(n) corresponds to a measured value of workload on step n; $W_{set}$ corresponds to an initial workload value, $k_1, k_2$ are coefficients for proportional and integral parts of the controller. Discrete integer values of intensity are obtained by rounding output Y(t) to the integer value: $Y_{current}$=ROUND(Y(n)), where ROUND( ) is the standard rounding function.

The whole system functions in the following way: If the system detects a change in workload value W(t), then in the case where workload W(t) is going down during specified time period P and passes through a threshold value T RH: W(t)−W(t+P)>=TRS, then the system turns on the controller. As a result, a lesson's intensity will be increased and, with delay workload value W(t) will also increase.

In case if W(t) is going up: W(t+P)−W(t)>=TRS, then the system will send a message to the student about increasing workload value in the form of a text message/graphic icon with numerical or symbolic value on computer screen overlay and/or sound.

In addition, to the message, the system may provide suggestions, such as breathing exercises, relaxation techniques, or others. The messages may depend on detected neurophysiological states, sensed by other sensors and a value of W(t) decrement. Then, after giving the student time period K(t) for normalization of W(t) value. K(t) value depends on value of W(t) decrement and student's personal history. Then if after time period K(t) value W(t) not normalized, the system turned on controller (2), which decrease lesson's intensity level.

In a further embodiment, learning optimization may be provided based on states of a student's cognitive alertness A(t) and level of engagement E(t), t-time. Differences between the embodiment and the previous embodiment are discussed below.

For calculating cognitive alertness and level of cognitive engagement, multiple sensors such as EEG, EKG, and GSR may be used. Conversion to the value of cognitive alertness A(t) may be done in according to the following regression type formula:

$$A(t-n) = k_1\alpha(t-n)/\theta(t-n) + k_2\gamma(t-n)/\alpha(t) + k_3\mathrm{ekg}(t-n) + k_4\mathrm{ekg}(t-n)^{1/2} + k_5\mathrm{gsr}(t-n) + k_6\mathrm{gsr}(t-n)^3, \quad n=0, 1, 2, \ldots, m$$

$$A(t) = \sum_{i=0}^{m} r_i A(t-i) \quad (3)$$

Where—$k_i$—conversion coefficients for different frequencies $\alpha(t), \beta(t), \gamma(t), \theta(t), \delta(t)$; ekg(t) refer to EKG sensors measurements; gsr(t)—GSR measurements; $r_i$—weight coefficients. We are using similar regression formula for conversion EEG, EKG, and GSR sensors measurements to level of engagement E(t) value.

Based on a student's cognitive alertness A(t) and level of engagement E(t) values a student's position in relation to optimal learning zone LZ(t) may be calculated by employing the following regression formula:

$$LZ(t-n) = \sum_{m=0}^{3} k_m^a A(t-n)^m + \sum_{m=0}^{3} k_m^e E(t-n)^m, n = 0, 1, 2, \ldots, s \quad (4)$$

$$LZ(t) = \sum_{i=0}^{m} r_i LZ(t-i)$$

Where—$k_i$—regression coefficients, $r_i$—weight coefficients.

An LZ(t) normal range is between $LZ_{min} <= LZ(t) <= LZ_{max}$.

In one embodiment for regulation of a lesson's intensity level, a proportional integral controller may be used:

$$Y(n) = k_1(LZ(n) - LZ_{set}) + \sum_{i=0}^{n} k_2(LZ(i) - LZ_{set}). \quad (5)$$

The whole system functioning is in accordance to the description for the previous embodiment, where workload value W(t) is replaced by learning zone value LZ(t).

Figure 4:
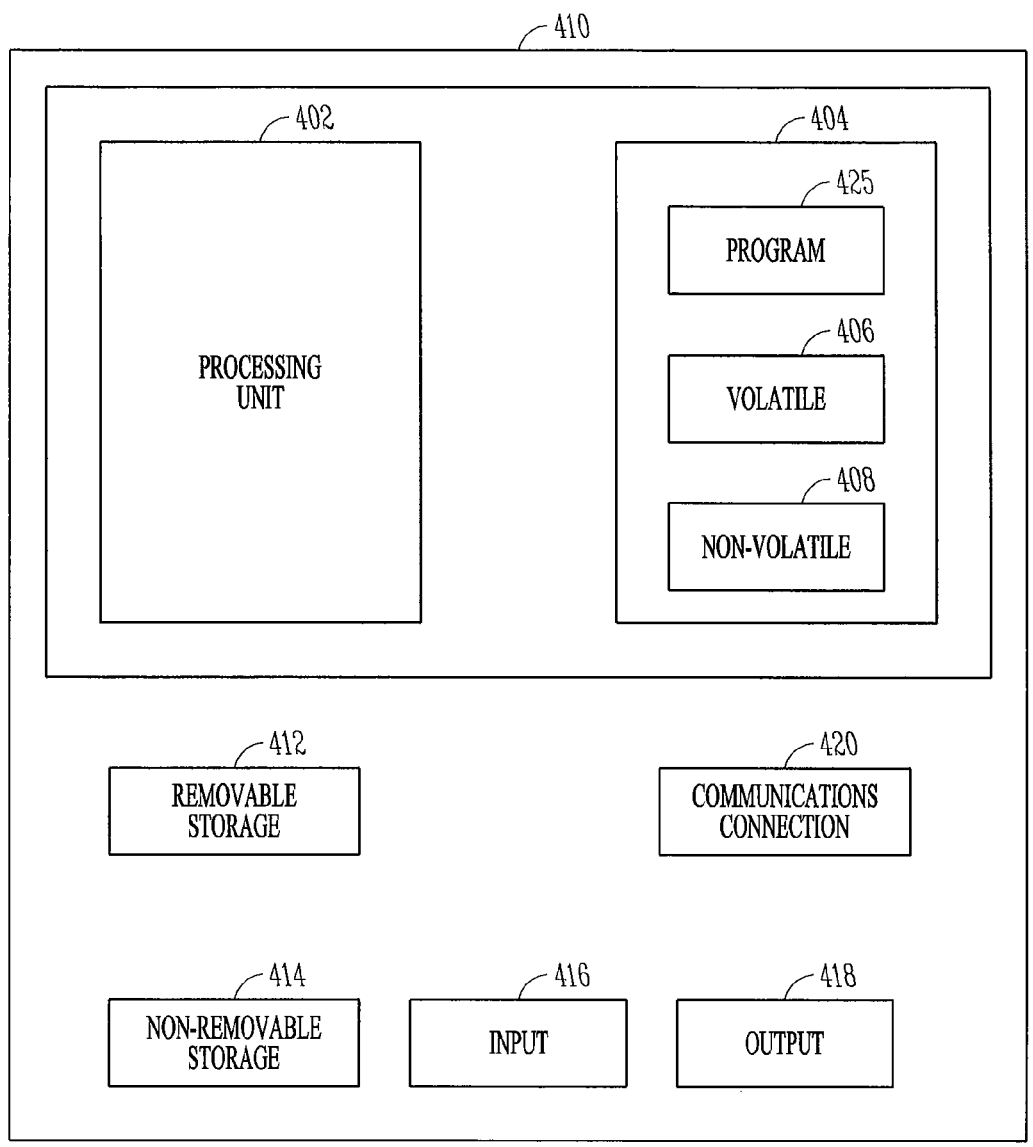
FIG. 4 is a block diagram of a specifically programmed computer system for executing methods and algorithms according to an example embodiment.

A block diagram of a computer system that executes programming for performing the above methods and algorithms is shown in FIG. 4. A general computing device in the form of a computer 410, may include a processing unit 402, memory 404, removable storage 412, and non-removable storage 414. Memory 404 may include volatile memory 406 and non-volatile memory 408. Computer 410 may include—or have access to a computing environment that includes—a variety of computer-readable media, such as volatile memory 406 and non-volatile memory 408, removable storage 412 and non-removable storage 414. Computer storage includes random access memory (RAM), read only memory (ROM), erasable programmable read-only memory (EPROM) & electrically erasable programmable read-only memory (EEPROM), flash memory or other memory technologies, compact disc read-only memory (CD ROM), Digital Versatile Disks (DVD) or other optical disk storage, magnetic cassettes, magnetic tape, magnetic disk storage or other magnetic storage devices, or any other medium capable of storing computer-readable instructions. Computer 410 may include or have access to a computing environment that includes input 416, output 418, and a communication connection 420. The computer may operate in a networked environment using a communication connection to connect to one or more remote computers. The remote computer may include a personal computer (PC), server, router, network PC, a peer device or other common network node, or the like. The communication connection may include a Local Area Network (LAN), a Wide Area Network (WAN) or other networks.

Computer-readable instructions stored on a computer-readable medium are executable by the processing unit 402 of the computer 410. A hard drive, CD-ROM, and RAM are some examples of articles including a computer-readable medium.

The Abstract is provided to comply with 37 C.F.R. §1.72(b) is submitted with the understanding that it will not be used to interpret or limit the scope or meaning of the claims.

The invention claimed is:

1. A system comprising:
a sensor to detect a neuro-physiological state of a student during a lesson;
a controller coupled to receive an output from the sensor to provide a communication if the student is outside a desired neuro-physiological state consistent with a desired learning zone and to provide a lesson intensity control signal as a function of the provided communication and sensed neuro-physiological state; and
a converter to convert the sensed neuro-physiological state of the student to cognitive parameters,
wherein the cognitive parameters are representative of cognitive workload, level of engagement, and alertness and wherein the lesson intensity is regulated using proportional integral control as a function of workload calculated from a sensed neuro-physiological state,
wherein the controller calculates workload as a function of amplitudes at multiple electroencephalograph frequencies, and
wherein the electroencephalograph frequencies include: $\alpha$ corresponding to a range 8-12 Hz, $\beta$ corresponding to a range of 12-30 Hz, $\gamma$ corresponding to a range of 30-100 Hz, $\theta$ corresponding to a range of 4-7 Hz and $\delta$ corresponding to a range 0-4 Hz, and wherein the controller is configured to calculate workload, W(t), according to the following formula:

$$W(t-n)=k_1\alpha(t-n)+k_2\beta(t-n)+k_3\gamma(t-n)+k_4\theta(t-n)+k_4\delta(t-n)+k_5\alpha(t-n)/\theta(t-n)+k_6\gamma(t-n)/\alpha(t), n=0, 1, 2, \ldots, m$$

$$W(t) = \sum_{i=0}^{m} r_i W(t-i)$$

where $k_i$ are conversion coefficients for different frequencies $\alpha(t), \beta(t), \gamma(t), \theta(t), \delta(t)$ and $r_i$ area weight coefficients.

2. The system of claim 1 wherein the controller is configured to calculate the lesson intensity value in accordance with:

$$Y(n) = k_1(W(n) - W_{set}) + \sum_{i=0}^{n} k_2(W(i) - W_{set})$$

where Y(n) corresponds to a lesson's intensity on step n, W(n) corresponds to a measured value of workload on step n, $W_{set}$ corresponds to an initial workload value, and $k_1, k_2$ are coefficients for proportional and integral parts of the controller.

3. The system of claim 1 wherein the sensor comprises an electroencephalograph.

4. The system of claim 1 wherein the sensor comprises multiple sensors selected from the group consisting of an electroencephalograph, electrocardiograph, galvanic skin response sensor, heart rate variability sensor and pupilometry sensor.

5. The system of claim 1 wherein the controller correlates the cognitive parameters to known patterns of such cognitive parameters to determine whether the student is within the desired learning zone.

6. The system of claim 5 wherein the known patterns are patterns specific to historical performance of the student.

7. The system of claim 1 wherein the communication comprises information on self regulation techniques to improve the neuro-physiological state.

8. The system of claim 7 wherein the controller modifies the lesson intensity as a function of change in neuro-physiological state over time in response to the communication.

9. The system of claim 8 wherein the lesson intensity control signal causes modification of at least one of volume or brightness of the learning environment.

10. The system of claim 8 wherein the lesson intensity control signal causes modification of the difficulty of the learning material presented to the student.

11. A system comprising:
a sensor to provide biosignals representative of a neuro-physiological state of a student;
a converter coupled to the sensor to convert the biosignals to learning zone digital values;
a learning environment for the student responsive to lesson intensity values; and
a controller coupled to the converter to receive learning zone digital values and to provide a communication to the student if the learning zone digital values are indicative of the student being outside a desired neuro-physiological state and to provide lesson intensity values as a function of the provided communication and sensed neuro-physiological state,
wherein the learning zone digital values are representative of cognitive workload, level of engagement, and alertness and wherein the lesson intensity is regulated using proportional integral control as a function of workload calculated from a sensed neuro-physiological state, wherein the controller calculates workload as a function of amplitudes at multiple electroencephalograph frequencies, and wherein the electroencephalograph frequencies include: α corresponding to a range 8-12 Hz, β corresponding to a range of 12-30 Hz, γ corresponding to a range of 30-100 Hz, θ corresponding to a range of 4-7 Hz and δ corresponding to a range 0-4 Hz, and wherein the controller is configured to calculate workload, W(t), according to the following formula:

$$W(t-n) = k_1\alpha(t-n) + k_2\beta(t-n) + k_3\gamma(t-n) + k_4\theta(t-n) + k_4\delta(t-n) + k_5\alpha(t-n)/\theta(t-n) + k_6\gamma(t-n)/\alpha(t), n=0, 1, 2, \ldots, m$$

$$W(t) = \sum_{i=0}^{m} r_i W(t-i)$$

where $k_i$ are conversion coefficients for different frequencies α(t), β(t), γ(t), θ(t), δ(t) and $r_i$ are weight coefficients.

12. The system of claim 11 wherein the controller provides lesson intensity values as a function of current and historical lesson intensity values.

13. The system of claim 11 wherein the learning environment is a computer controlled learning environment.

14. The system of claim 11 wherein the learning environment is a computer simulation.

15. The system of claim 11 wherein the learning environment is a classroom.

16. The system of claim 11 wherein the sensor comprises multiple sensors selected from the group consisting of an electroencephalograph, electrocardiograph, galvanic skin response sensor, heart rate variability sensor and pupilometry sensor.

17. The system of claim 11 wherein the communication comprises information on self regulation techniques to improve the neuro-physiological state.

18. The system of claim 11 wherein the controller modifies the lesson intensity as a function of change in neuro-physiological state over time in response to the communication.

19. A computer implemented method comprising:
receiving biosignals representative of a neuro-physiological state of a student;
determining a current neuro-physiological state from the received biosignals;
converting the determined neuro-physiological state to cognitive parameters;
providing feedback to the student as a function of the neuro-physiological state;
detecting if the neuro-physiological state of the student has changed following provision of the feedback;
modifying a lesson intensity value as a function of the neuro-physiological state of the student following provision of the feedback; and
providing the modified lesson intensity value to a learning environment,
wherein the cognitive parameters are representative of cognitive workload, level of engagement, and alertness and wherein the lesson intensity is regulated using proportional integral control as a function of workload calculated from a sensed neuro-physiological state,
wherein the controller calculates workload as a function of amplitudes at multiple electroencephalograph frequencies, and
wherein the electroencephalograph frequencies include: α corresponding to a range 8-12 Hz, β corresponding to a range of 12-30 Hz, γ corresponding to a range of 30-100 Hz, θ corresponding to a range of 4-7 Hz and δ corresponding to a range 0-4 Hz, and wherein the controller is configured to calculate workload, W(t), according to the following formula:

$$W(t-n) = k_1\alpha(t-n)k_2\beta(t-n) + k_3\gamma(t-n) + k_4\theta(t-n) + k_4\delta(t-n) + k_5\alpha(t-n)/\theta(t-n) + k_6\gamma(t-n)/\alpha(t), n=0, 1, 2, \ldots, m$$

$$W(t) = \sum_{i=0}^{m} r_i W(t-i)$$

where $k_i$ are conversion coefficients for different frequencies α(t), β(t), γ(t), θ(t), δ(t) and $r_i$ are weight coefficients.

* * * * *